US010278806B2

(12) United States Patent
McMahon et al.

(10) Patent No.: US 10,278,806 B2
(45) Date of Patent: May 7, 2019

(54) URETERAL STENT AND METHOD

(71) Applicant: BAYLOR UNIVERSITY, Waco, TX (US)

(72) Inventors: Charles Wesley McMahon, Waco, TX (US); Corrine Audrey Nief, Durham, NC (US); Danielle Rae Schmidt, Salt Lake City, UT (US); Lisa Jin Choe, Philadelphia, PA (US); Maria Guadalupe Aponte, Cypress, TX (US); Sara L. Pelayo, San Antonio, TX (US)

(73) Assignee: BAYLOR UNIVERSITY, Waco, TX (US)

( * ) Notice: Subject to any disclaimer, the term of this patent is extended or adjusted under 35 U.S.C. 154(b) by 0 days.

(21) Appl. No.: 15/443,248

(22) Filed: Feb. 27, 2017

(65) Prior Publication Data

US 2018/0243073 A1     Aug. 30, 2018

(51) Int. Cl.
*A61F 2/04*     (2013.01)
*A61M 27/00*     (2006.01)

(52) U.S. Cl.
CPC ............ *A61F 2/04* (2013.01); *A61M 27/002* (2013.01); *A61M 27/008* (2013.01);
(Continued)

(58) Field of Classification Search
CPC .......... A61F 2/04; A61F 2/042; A61M 39/24; A61M 2039/2406; A61M 2039/2413; A61M 2039/242; A61M 2039/2426; A61M 2039/2433; A61M 2039/244; A61M 2039/2446; A61M 2039/2453; A61M 2039/246; A61M 2039/2466; A61M 27/00; A61M 27/002; A61M 27/006; A61M 27/008; A61M 2027/004; F16K 15/144;
(Continued)

(56) References Cited

U.S. PATENT DOCUMENTS 178,253 A * 6/1876 Stacy et al. ........... F16K 15/144
                                                        137/496
568,362 A * 9/1896 MacSpadden .......... B60C 29/04
                                                        152/429
(Continued)

FOREIGN PATENT DOCUMENTS

EP         0516189 A1    12/1992
WO       WO89/05127      6/1989

*Primary Examiner* — Andrew M Iwamaye
(74) *Attorney, Agent, or Firm* — Jackson Walker, LLP (57) ABSTRACT

The present disclosure provides a ureteral stent, having an elongated tube configured to be inserted into a ureter; a first end having a retainer portion configured to be inserted into a kidney; and a second end configured to be inserted into a bladder, the second end having an anchor portion fluidicly coupled with the first end, the second end having a collapsible wall expandable to a cross-sectional size greater than the cross-sectional size of the ureter; a tube port fluidicly coupled with the first end; and a flapper valve having at least two valve ends coupled to the anchor portion over the port; and a flexible middle portion between the at least two valve ends configured to flex toward the port to cover the port with a predetermined amount of ambient pressure in the bladder and flex away from the port when ambient pressure is lower than the predetermined amount.

10 Claims, 9 Drawing Sheets

(52) U.S. Cl.
CPC . *A61F 2002/048* (2013.01); *A61F 2230/0067* (2013.01); *A61F 2230/0069* (2013.01); *A61F 2230/0093* (2013.01)

(58) Field of Classification Search
CPC ......... Y10T 137/2617; Y10T 137/7374; Y10T 137/2587; Y10T 83/8861; Y10T 137/5994
USPC ........................................................ 137/851
See application file for complete search history.

(56) References Cited

U.S. PATENT DOCUMENTS

| | | | | |
|---|---|---|---|---|
| 733,152 A * | 7/1903 | Chisholm | ............ | A61M 39/24 604/247 |
| 2,195,292 A * | 3/1940 | Albertson | ............... | F16K 15/16 137/527 |
| 2,768,639 A * | 10/1956 | Stilwell | .................. | E03C 1/108 137/217 |
| 2,793,649 A * | 5/1957 | Hamer | ...................... | F16T 1/14 137/204 |
| 3,123,096 A * | 3/1964 | Notaro et al. | ........ | F04B 39/102 137/851 |
| 3,179,309 A * | 4/1965 | Cope | ...................... | B65D 83/42 137/851 |
| 3,263,700 A * | 8/1966 | Toland | ................... | B62D 25/24 137/851 |
| 4,212,304 A | 7/1980 | Finney | | |
| 4,531,933 A | 7/1985 | Norton et al. | | |
| 5,019,102 A | 5/1991 | Hoene | | |
| 5,380,270 A | 1/1995 | Ahmadzadeh | | |
| 6,357,473 B1 * | 3/2002 | Porter | .................... | B60H 1/249 137/512.15 |
| 6,991,614 B2 | 1/2006 | McWeeney et al. | | |
| 8,142,386 B2 | 3/2012 | McWeeney | | |
| 2003/0106589 A1 * | 6/2003 | Basso | ................. | B65D 77/225 137/512.15 |
| 2005/0155657 A1 * | 7/2005 | Kach | ................... | F04B 53/1062 137/859 |
| 2005/0240280 A1 * | 10/2005 | Aliski | ........................ | A61F 2/04 623/23.68 |
| 2006/0177330 A1 * | 8/2006 | Hargraves | ........... | F04B 39/1073 417/566 |
| 2009/0065067 A1 * | 3/2009 | Bushman | ................. | A61C 1/16 137/217 |
| 2009/0173391 A1 * | 7/2009 | Choksi | ................. | F16K 15/144 137/14 |
| 2011/0079299 A1 * | 4/2011 | Yuguchi | ................ | F16K 15/144 137/511 |
| 2012/0192977 A1 * | 8/2012 | Tsao | .................... | A61M 1/0001 137/843 |

* cited by examiner

URETERAL STENT AND METHOD

CROSS REFERENCE TO RELATED APPLICATIONS

Not applicable.

STATEMENT REGARDING FEDERALLY SPONSORED RESEARCH OR DEVELOPMENT

Not applicable.

REFERENCE TO APPENDIX

Not applicable.

BACKGROUND OF THE INVENTION

Field of the Invention

The disclosure generally relates to medical stents. More specifically, the disclosure relates to medical stents for bladders.

Description of the Related Art

The kidneys are one of the most important components of the urinary system. They remove impurities from the blood and help maintain water balance and the composition of electrolytes. Each kidney is connected to the bladder through a ureter, a thin, hollow tube that is elastic. On average, each ureter stretches about 12 inches and its widest portion measures approximately 0.5 inches in circumference. Urine is moved through the ureter by peristaltic (wave-like) movements that originate from the electrical activity derived from pacemaker sites in the proximal portion of the bladder. According to Campbell's Urology, resting ureteral pressure is approximately 0 to 5 cm H2O, and superimposed ureteral contractions ranging from 20 to 80 cm H2O occur six times per minute. These peristaltic contractions cause the bolus of urine to move through the ureter. The ureters connect to the very sensitive, triangular area on the bladder floor called the trigone. A valve-like mucous membrane inside the ureter keeps the urine inside the bladder and prevents it from traveling back towards the kidney, forming the ureterovesical junction (UVJ). Having an obstruction at the UVJ can impede the movement of urine to the bladder.

The bladder is a hollow organ, lined mainly with smooth muscle, which stores urine until it is expelled. The ureters enter the bladder at a diagonal angle and intersect with the trigone area. The opening to the urethra is located at the distal end of the trigone, also known as the "neck" of the bladder. As the bladder fills with urine, its walls stretch and the muscles that line it relax. On average, a healthy adult can comfortably hold 14-20 ounces of urine inside their bladder. Once the bladder is full, the bladder releases urine through a process known as micturition. Urine is transported from the kidney into the bladder every 10 to 15 seconds until the bladder is full.

Many people are affected by kidney stones and ureteral obstructions. A common treatment for such conditions is the insertion of a ureteral stent. A ureteral stent is a tube-like device that is inserted into the ureter to provide ureteral rigidity and allow the passage of urine.

Figure 1:
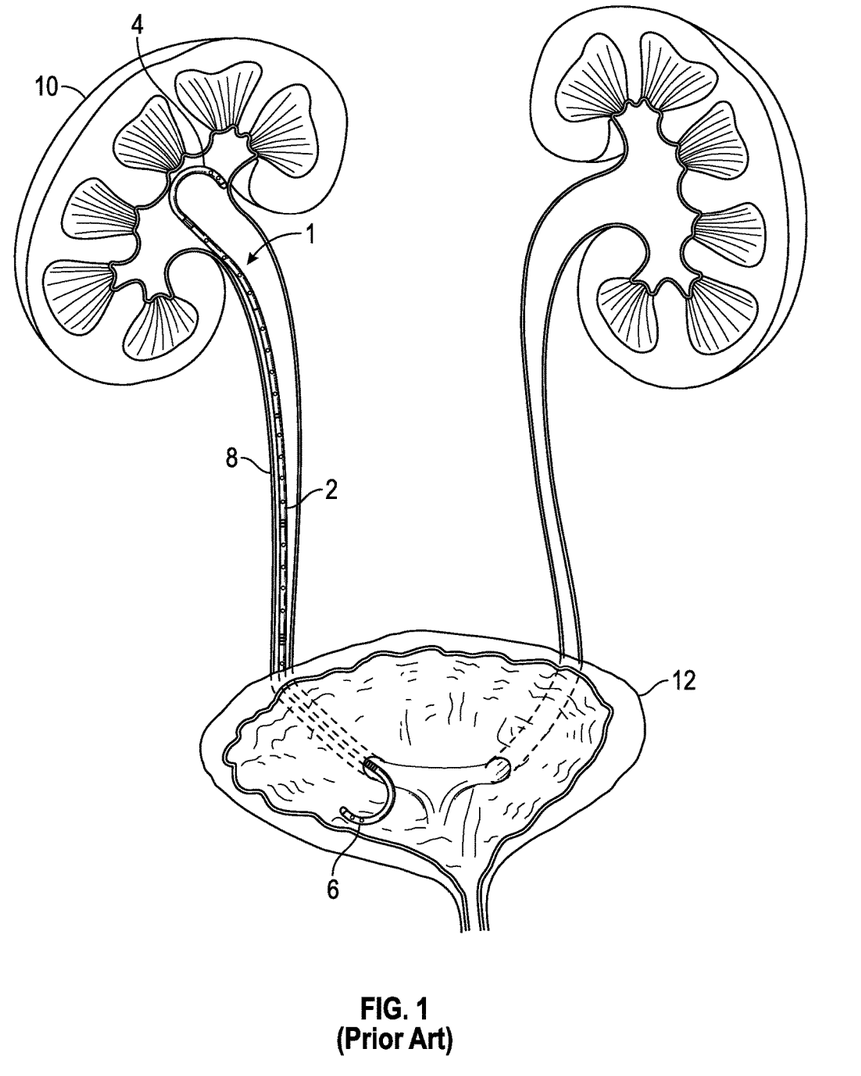
FIG. 1 is a schematic front view of a known ureteral stent.

As exemplary commonly used ureteral stents is shown in FIG. 1 that is based on U.S. Pat. No. 4,212,304. The exemplary known stent 1 has two flexible curved ends 4 and 6 on a tube 2. Generally, both ends are straightened for insertion from an external position of the body through the urethra into the bladder 12 and then a first curved end 4 can be further inserted through the ureter 8 into a kidney 10. After insertion, the curved end 4 can be released to regain its curved shape to be retained within the kidney. The other end 6 can be released to regain its curved shape to be retained within the bladder. Although this stent provides rigidity and drainage, it is known to cause unwanted side effects, such as bladder irritation, stent movement or migration, and urine reflux caused by the stent allowing urine to flow backward during urination to cause pain from the kidney.

Figure 2A:
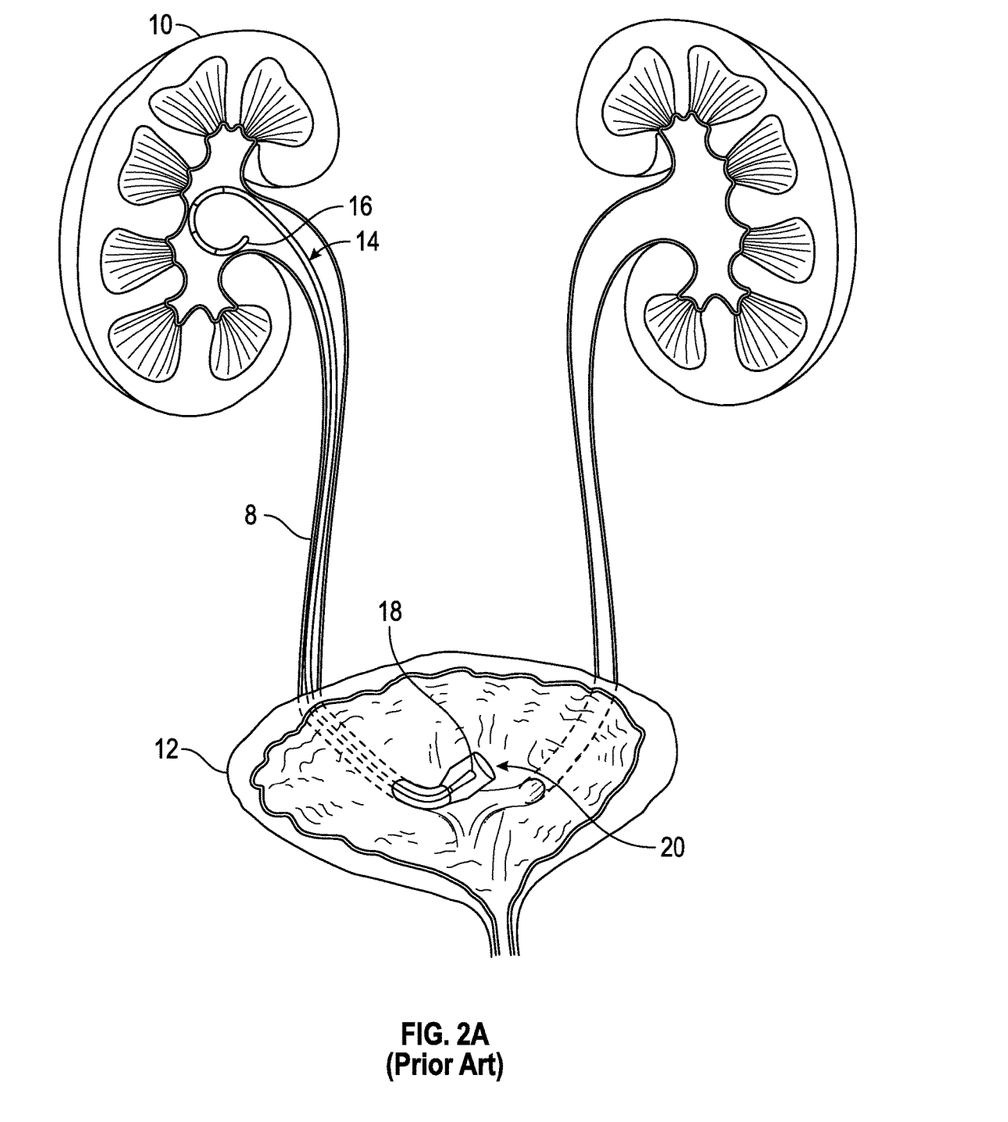
FIG. 2A is a schematic front view of another known ureteral stent inserted into the ureter between a kidney and a bladder.
Figure 2B:
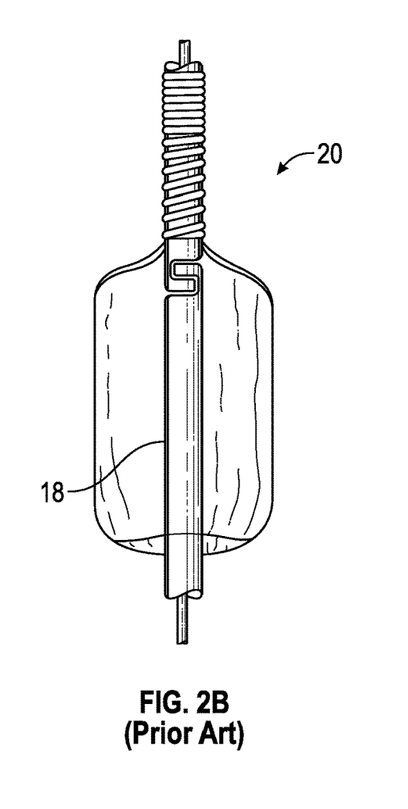
FIG. 2B is an enlarged schematic front view of a portion of the ureteral stent in the bladder of FIG. 2A.

FIGS. 2A and 2B are based on U.S. Pat. No. 5,380,270 and show another type of a known ureteral stent. The stent 14 has a similar curved end 16 as described above and is used for insertion through the ureter 8 into the kidney(s) 10, and a second end 18 has a retainer system 20 to be retained in the bladder 12.

Figure 3:
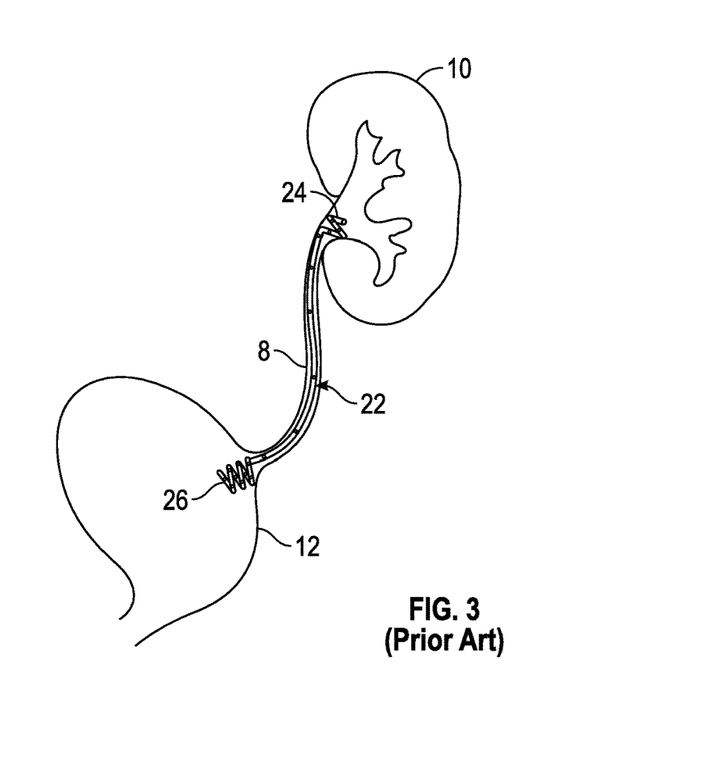
FIG. 3 is a schematic front view of another known ureteral stent inserted into the ureter.

FIG. 3 is based on U.S. Pat. No. 4,531,933 and shows yet another type of a known ureter stent with helical coils on each end. The stent 22 has two ends with helical coils that can be unwound for insertion through the urethra and one end 24 further inserted through the ureter 8 and allowed to resume its wound shape after insertion into the kidney 10. Another end 26 of the stent 22 has a helical coil and can be remain in the bladder 12

Figure 4A:
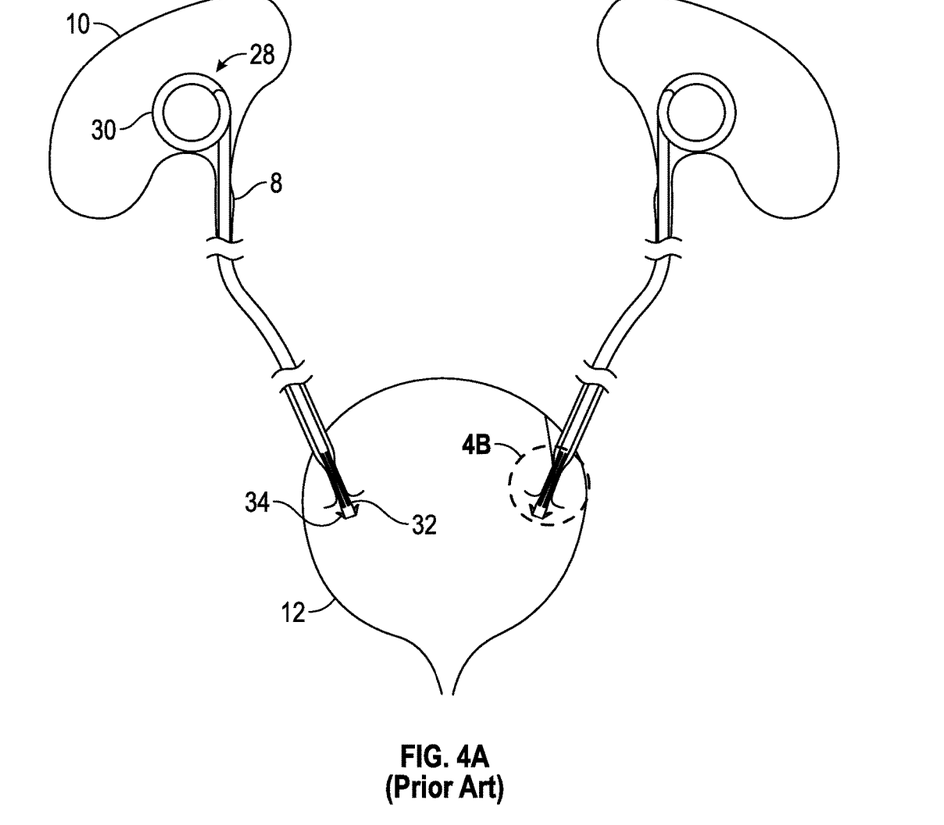
FIG. 4A is a schematic front view of another known ureteral stent inserted into the ureters.
Figure 4B:
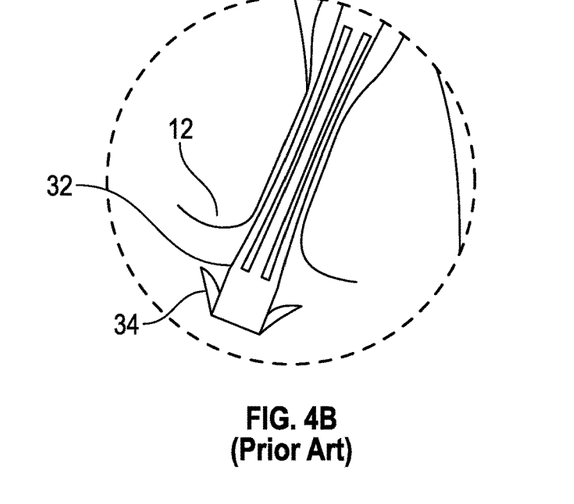
FIG. 4B is an enlarged schematic front view of a portion of the ureteral stent in the bladder of FIG. 4A.
Figure 4C:
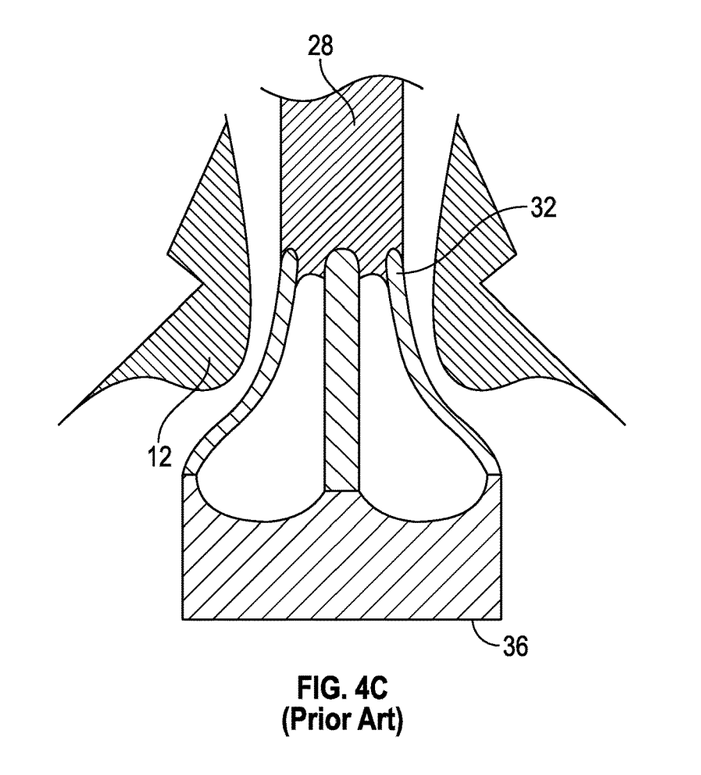
FIG. 4C is an enlarged schematic front view of a variation of the portion of the ureteral stent in the bladder of FIG. 4A.

FIGS. 4A and 4B are based on U.S. Pat. No. 8,142,386 and show another type of a known ureter stent 28 with a curved end 30 inserted into the kidney 10 as described above, and a second end 32 with a barbed hook 34 extending laterally from the end in the bladder 12 to keep the stent from migrating up into the ureter 8. FIG. 4C shows a further variation in this patent with an expanded portion 36 at the end 30 to keep the stent 28 in the bladder 12.

Figure 5A:
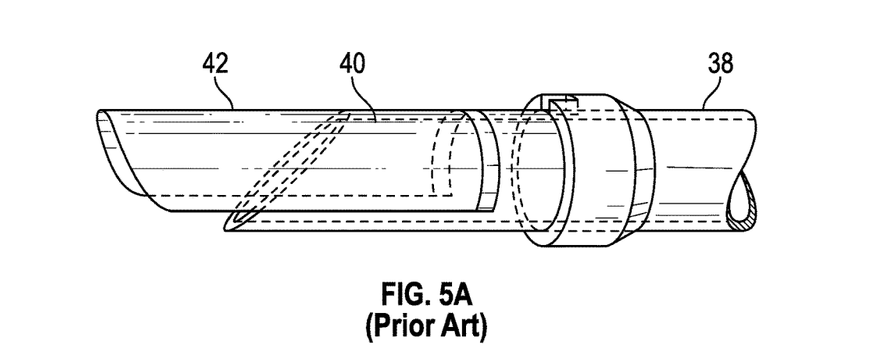
FIG. 5A is a schematic side view of another known ureteral stent.
Figure 5B:
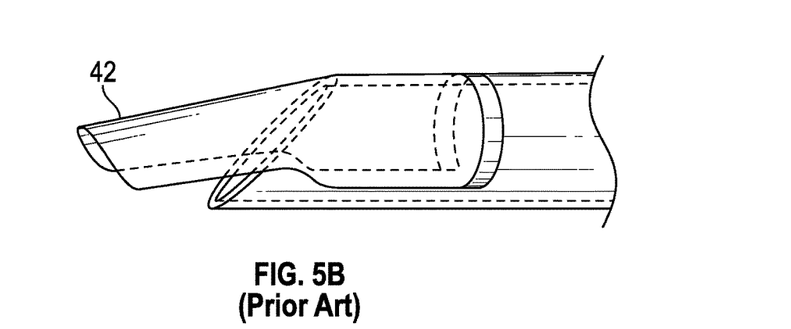
FIG. 5B is a schematic side view of the ureteral stent of FIG. 5A in a partially restricted position.
Figure 5C:
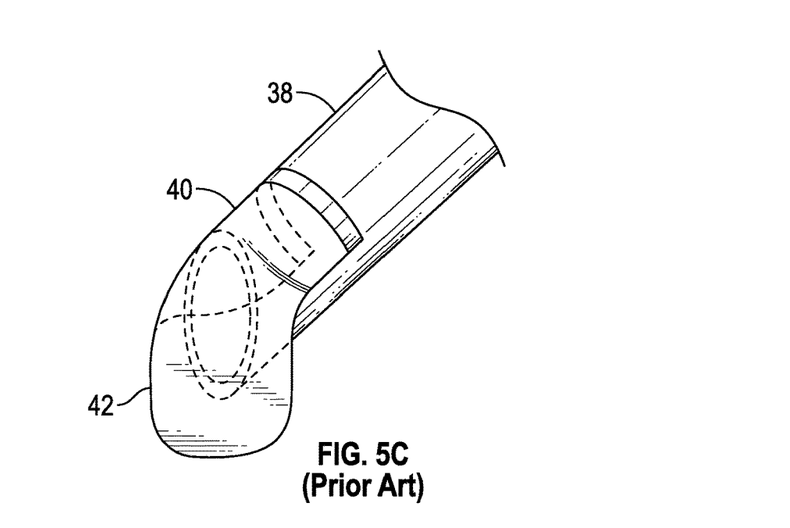
FIG. 5C is a schematic side view of the ureteral stent of FIG. 5A in a restricted position.

FIGS. 5A, 5B, and 5C are based on U.S. Pat. No. 5,019,102 and show another type a known ureter stent 38 with a hood valve 42 over an end 40 of a ureteral catheter located in the bladder. When the bladder is empty and little or no bladder pressure D, the valve is open. As bladder pressure increases, the hood valve 42 is progressively deformed until it lies upon a port on the end 40 and limits reflux up the catheter.

There remains a need for an improved ureteral stent and associated method of use.

BRIEF SUMMARY OF THE INVENTION

The present disclosure provides a ureteral stent, having an elongated tube configured to be inserted into a ureter; a first end having a retainer portion configured to be inserted into a kidney; and a second end configured to be inserted into a bladder, the second end having an anchor portion fluidicly coupled with the first end, the second end having a collapsible wall expandable to a cross-sectional size greater than the cross-sectional size of the ureter; a tube port fluidicly coupled with the first end; and a flapper valve having at least two valve ends coupled to the anchor portion over the port; and a flexible middle portion between the at least two valve ends configured to flex toward the port to cover the port with a predetermined amount of ambient pressure in the bladder and flex away from the port when ambient pressure is lower than the predetermined amount.

The present invention also provides a method of use for a ureteral stent for flow between a kidney and a bladder through a ureter, the ureter having a first end, an elongated tube coupled to the first end, the first end having a retainer portion, and a second end coupled to the elongated tube distal from the first end, the second end having an anchor portion having a collapsible wall with a flapper valve having at least two valve ends coupled to the wall and a flexible portion between the at least two valve ends to reciprocally at least partially cover and uncover a tube port on the second end from the elongated tube, the method comprising: reforming the retainer portion of the first end; inserting the retainer portion of the first end into a channel of an instrument; inserting the instrument into a urethra; advancing the first end through the urethra and into the bladder; advancing the first end through the ureter and into the kidney with the elongated tube disposed in the ureter and the anchor portion in a collapsed state disposed in the bladder; retracting the instrument from the kidney; allowing the retainer portion of the first end to assume a rest state in the kidney; retracting the instrument from the ureter and at least partially retracting the instrument from the bladder; and allowing the anchor portion to assume a rest state that is larger than the collapsed state and the flexible portion of the flapper valve to at least partially uncover the tube port when ambient pressure in the bladder is below a predetermined amount.

DETAILED DESCRIPTION

The Figures described above and the written description of specific structures and functions below are not presented to limit the scope of what Applicant has invented or the scope of the appended claims. Rather, the Figures and written description are provided to teach any person skilled in the art to make and use the inventions for which patent protection is sought. Those skilled in the art will appreciate that not all features of a commercial embodiment of the inventions are described or shown for the sake of clarity and understanding. Persons of skill in this art will also appreciate that the development of an actual commercial embodiment incorporating aspects of the present disclosure will require numerous implementation-specific decisions to achieve the developer's ultimate goal for the commercial embodiment. Such implementation-specific decisions may include, and likely are not limited to, compliance with system-related, business-related, government-related and other constraints, which may vary by specific implementation or location, or with time. While a developer's efforts might be complex and time-consuming in an absolute sense, such efforts would be, nevertheless, a routine undertaking for those of ordinary skill in this art having benefit of this disclosure. It must be understood that the inventions disclosed and taught herein are susceptible to numerous and various modifications and alternative forms. The use of a singular term, such as, but not limited to, "a," is not intended as limiting of the number of items. Further, the various methods and embodiments of the system can be included in combination with each other to produce variations of the disclosed methods and embodiments. Discussion of singular elements can include plural elements and vice-versa. References to at least one item may include one or more items. Also, various aspects of the embodiments could be used in conjunction with each other to accomplish the understood goals of the disclosure. Unless the context requires otherwise, the term "comprise" or variations such as "comprises" or "comprising," should be understood to imply the inclusion of at least the stated element or step or group of elements or steps or equivalents thereof, and not the exclusion of a greater numerical quantity or any other element or step or group of elements or steps or equivalents thereof. The device or system may be used in a number of directions and orientations. The order of steps can occur in a variety of sequences unless otherwise specifically limited. The various steps described herein can be combined with other steps, interlineated with the stated steps, and/or split into multiple steps. Some elements are nominated by a device name for simplicity and would be understood to include a system or a section, such as a processor would encompass a processing system of related components that are known to those with ordinary skill in the art and may not be specifically described.

The present disclosure provides a ureteral stent, having an elongated tube configured to be inserted into a ureter; a first end having a retainer portion configured to be inserted into a kidney; and a second end configured to be inserted into a bladder, the second end having an anchor portion fluidicly coupled with the first end, the second end having a collapsible wall expandable to a cross-sectional size greater than the cross-sectional size of the ureter; a tube port fluidicly coupled with the first end; and a flapper valve having at least two valve ends coupled to the anchor portion over the port; and a flexible middle portion between the at least two valve ends configured to flex toward the port to cover the port with a predetermined amount of ambient pressure in the bladder and flex away from the port when ambient pressure is lower than the predetermined amount.

In general, it is desirable that the stent design be made of biocompatible materials and be scalable to fit people of different sizes. In at least one embodiment, the stent can be scaled within two standard deviations of the average height of a ureter length. Further, the stent can be designed to allow total fluid flow of at least 25±1 mL/min from the proximal end to the distal end of the ureter based on medical data, and to fit inside the working space of a scope, generally at 10 French (3.33 mm) or smaller for stent insertion. Also, the stent can be designed to fit through an average urethra diameter of 24.5±0.5 French (8.17±0.17 mm) for stent removal. Advantageously, the stent reduces irritation, migration, and reflux into the ureter.

Figure 6A:
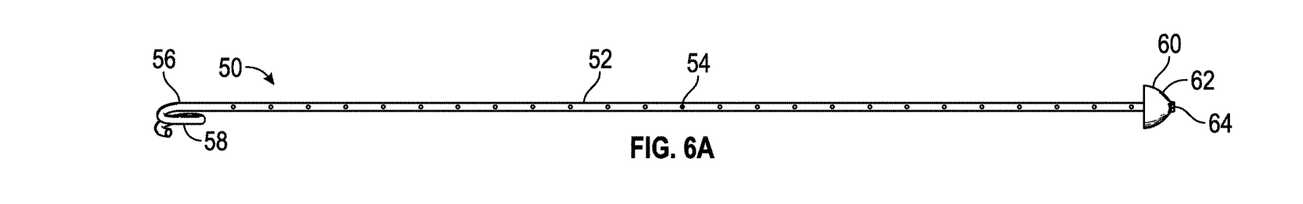
FIG. 6A is a schematic front view of an exemplary ureter stent according to the invention.
Figure 6B:
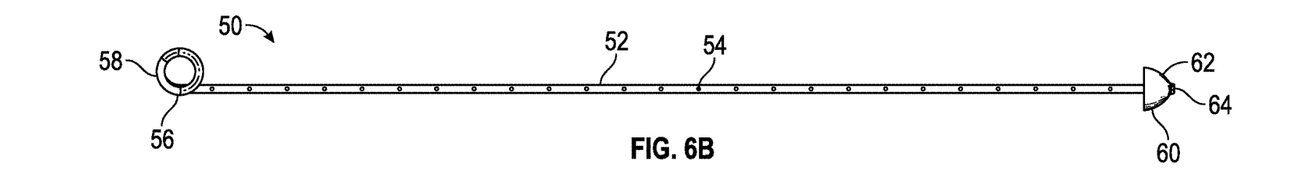
FIG. 6B is a schematic side view of the exemplary ureter stent shown in FIG. 6A.
Figure 6C:
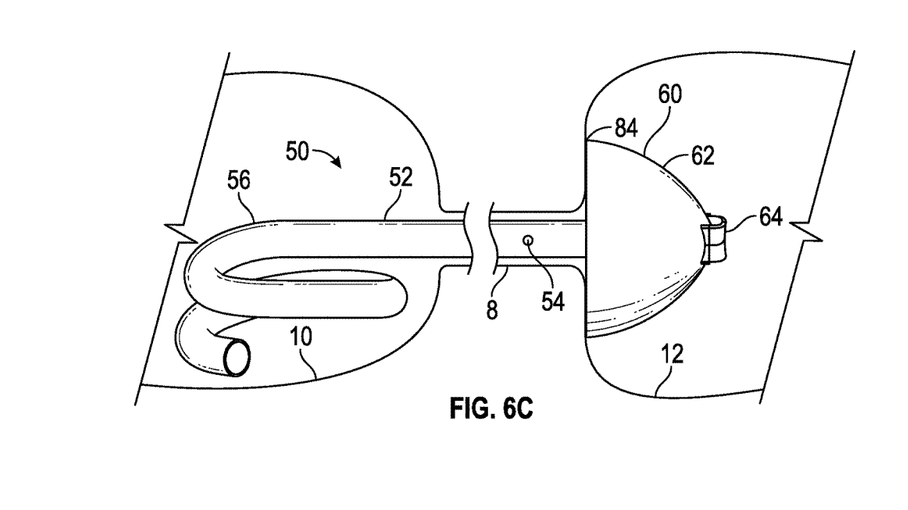
FIG. 6C is an enlarged schematic side view of the exemplary ureter stent shown in FIG. 6B.

FIG. 6A is a schematic front view of an exemplary ureter stent according to the invention. FIG. 6B is a schematic side view of the exemplary ureter stent shown in FIG. 6A. FIG. 6C is an enlarged schematic side view of the exemplary ureter stent shown in FIG. 6B. The stent 50 includes an elongated tube 52 with optional lateral openings 54 along the length. The openings provide for flow in and out of the flow path inside the tube 52 and the flow path around the tube but inside the ureter 8 that forms an annulus around the tube when the stent is placed in the ureter. The stent 50 includes a first end 56 coupled to the tube 52 and having a retainer portion 58. The retainer portion 58 can be shaped in the form of a curved portion such as shown in FIGS. 1, 2A, and 4A, or the helical coil shown in FIG. 3, or other retainer shapes that can be pushed through the ureter 8 and then expanded into the kidney 10. The stent 50 further includes a second end 60 coupled to the tube 52 and having an anchor portion 62. The anchor portion 62 is configured to be inserted into a bladder 12 and remain in the bladder and the first end 56 can be inserted through the ureter 8 into the kidney 12. The anchor portion 62 has a smaller cross section in the bladder than at least some of the commercially available stents, such as those with the curved ends shown in FIG. 1, and is believed to cause less bladder irritation. The anchor portion 62 can be of various shapes. In the exemplary embodiment, the anchor portion includes an enlarged base 84 that can be lodged adjacent a wall of the bladder in proximity to the entrance to the ureter when the tube 52 is inserted in the ureter. Advantageously, the cross-sectional size of the base 11 is generally larger when expanded than an average cross-sectional diameter of the ureter even when the ureter is expanded due to an obstruction in the ureter. For example, an exemplary base could be 11 mm in diameter when deployed in the bladder. Further, the wall of the anchor portion 62 can be formed with a sloping surface from the base to the tube port to lessen the volume of the anchor portion in the bladder. The anchor portion 62 further includes a flapper valve 64 coupled to an end of the anchor portion 62 is described in more detail below.

One or more portions of the stent 50 can be made of a biocompatible material. Biocompatible materials include silicone, polyurethane, and other biocompatible polymers. Different materials can be used for different portions. For example, for the distal end that rests in the bladder, a high coil retention rate, low elastic modulus, and low coefficient of friction are advantageous. For the proximal end that rests in the kidney and tube of the stent, a high coil retention rate, high tensile strength, and low coefficient of friction are advantageous. The coil retention rate describes the materials' ability to ensure the desired shape is held. The elastic modulus reflects the material's ability to deform in the scope. The coefficient of friction is considered to understand the ease of passage of the stent through the scope. The tensile strength reflects the materials ability to prevent fracture.

Figure 7A:
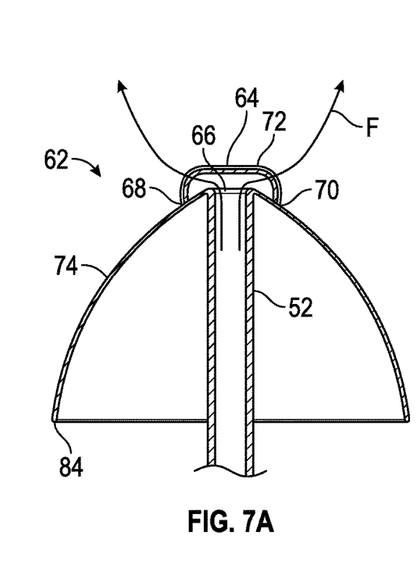
FIG. 7A is a schematic cross section view of a portion of the exemplary ureter stent shown in FIG. 6A.
Figure 7B:
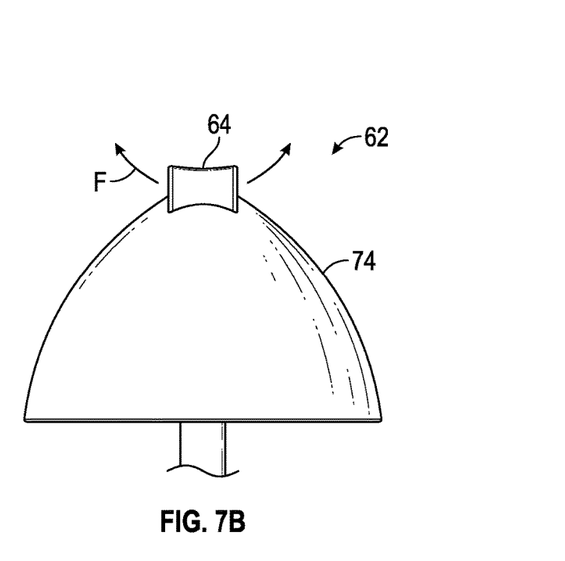
FIG. 7B is an enlarged schematic side view of the portion of the exemplary ureter stent shown in FIG. 7A.
Figure 7C:
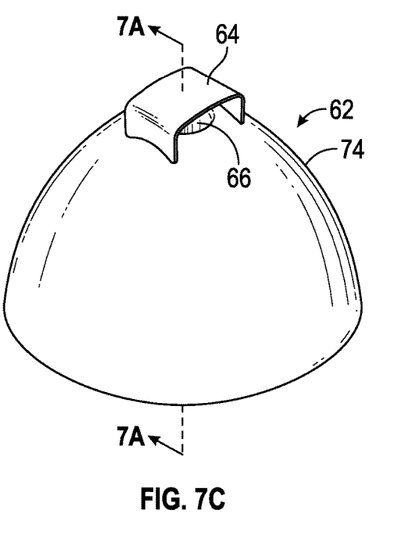
FIG. 7C is an enlarged schematic perspective view of the portion of the exemplary ureter stent shown in FIG. 7A.
Figure 7D:
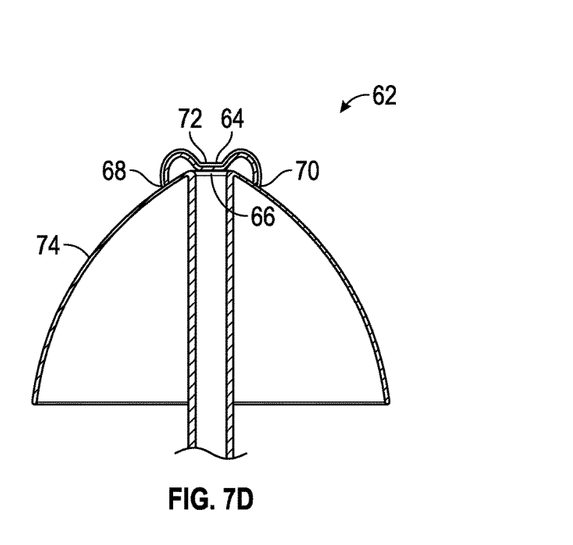
FIG. 7D is an enlarged schematic perspective view of the portion of the exemplary ureter stent shown in FIG. 7A in a closed condition

FIG. 7A is a schematic cross section view of a portion of the exemplary ureter stent shown in FIG. 6A in an open condition. FIG. 7B is an enlarged schematic side view of the portion of the exemplary ureter stent shown in FIG. 7A in an open condition. FIG. 7C is an enlarged schematic perspective view of the portion of the exemplary ureter stent shown in FIG. 7A in an open condition. FIG. 7D is an enlarged schematic perspective view of the portion of the exemplary ureter stent shown in FIG. 7A in a closed condition. The anchor portion 62 generally includes a collapsible wall 74 to reduce a cross section of the anchor portion 62 for insertion into the bladder, such as through the urethra, described above. The tube 52 can extend into the anchor portion 62, terminate in the anchor portion 62, and form a tube port 66 to establish the flow path F between the tube 52 and the bladder in which the anchor portion 62 is located after installation of the stent.

A flapper valve 64 is coupled to the wall 74 over the tube port 66. A valve end 68 is coupled to the wall 74 on one side of the tube port 66, and a valve end 70 is coupled to the wall 74 distally from the valve end 68 relative to the tube port 66. A flexible portion 72 is disposed between the valve end 68 and valve end 70. The flexible portion can reciprocally move between an elevated open position shown in FIGS. 7A-7C and a lowered closed position relative to the tube port 66 shown in FIG. 7D (relative to the orientation of the FIGS. 7A-7D). If there is little pressure in the bladder, the flexible portion 72 can elevate to a rest position and allow the flow F to proceed into the bladder from the tube 52 that are fluidicly coupled to the kidney 10. When the bladder is filling or full, the bladder pressure increases and presses the flexible portion 72 into a lowered position that covers the tube port 66. The flexible portion 72 can resume its rest state in an elevated position when the bladder is emptied and the bladder pressure is reduced. In the rest state, the flow path F can flow fluid from the ureter into the bladder. The valve ends 68 and 70 assist in stabilizing the reciprocal movement of the flapper valve 64 by both ends being coupled to the wall 74 over the tube port 66.

Figure 8:
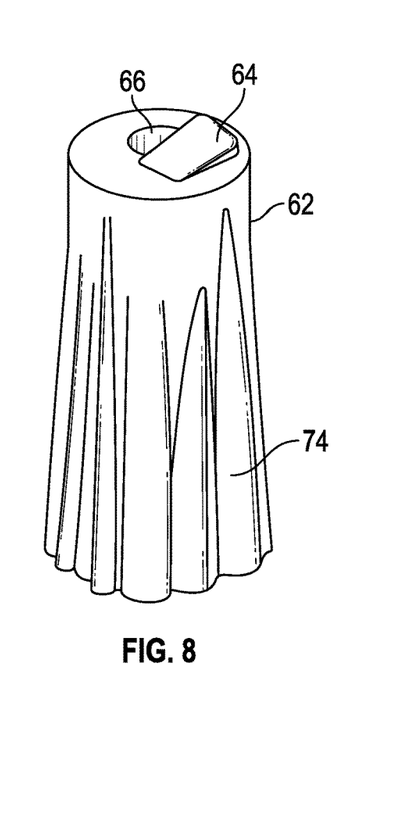
FIG. 8 is a schematic perspective view of a collapsible portion of an exemplary ureter stent.

FIG. 8 is a schematic perspective view of a collapsible wall 74 of an exemplary ureter stent. To reduce the cross-section of the anchor portion 62, the wall 74 can be collapsible. In some embodiments, the wall can be collapsed by folding. In other embodiments, the wall can be collapsible by elastic stretching of the wall material. Other collapsible methods can be made, and those shown and described are merely exemplary.

Figure 9:
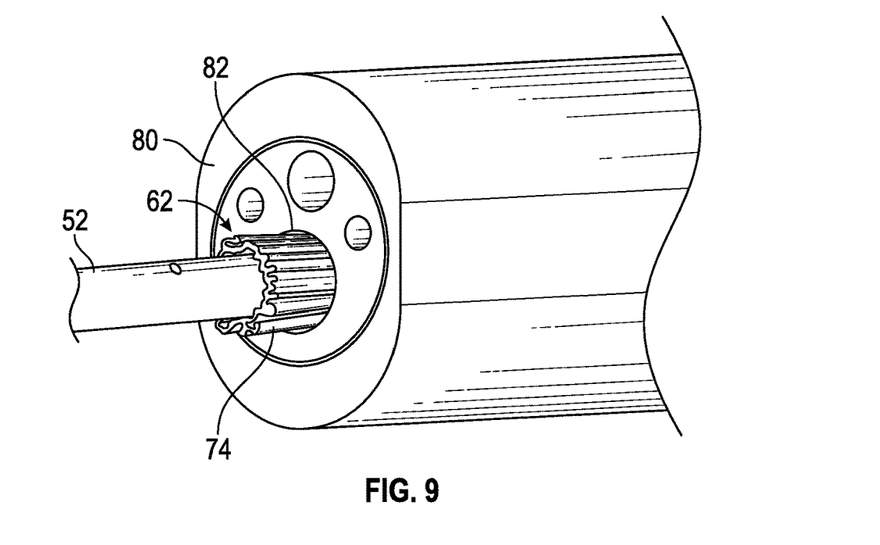
FIG. 9 is a schematic perspective view of the collapsible portion of the exemplary ureter stent shown in FIG. 8 that is partially inserted into a cystoscope working channel.

FIG. 9 is a schematic perspective view of the collapsible portion of the exemplary ureter stent shown in FIG. 8 that is partially inserted into a cystoscope working channel. The cystoscope or other suitable medical instrument can be used to deploy the stent through the bladder into the ureter. The collapsible wall 74 can be inserted into an instrument for insertion into the bladder. For example, a cystoscope 80 having a working channel 82 can be used to insert the tube 52 followed by the anchor portion 62 with the collapsible wall 74 through a urethra and into the bladder.

In operation, an exemplary use of the stent can be described as follows. An operator, typically a medical personnel, reforms the retainer portion of the first end, such as by straightening out the curved portion of the retainer portion (although other shapes of retainer portions are contemplated). The operator can insert the retainer portion of the first end into a channel of an instrument, such as a cystoscope and the instrument can be inserted into a urethra. The operator can advance the first end through the urethra and into the bladder. As the first end advances, the elongated tube and second end with the anchor portion also advances until the anchor portion is collapsed to enter the instrument channel. The operator can further advance the first end through the ureter and into the kidney with the elongated tube disposed in the ureter and the anchor portion in a collapsed state disposed in the bladder. After the stent is positioned, the operator can retract the instrument from the kidney, and allow the retainer portion of the first end to assume a rest state in the kidney. In the rest state, the retainer portion is formed in a manner that resists re-entry back into the ureter. The operator can further retract the instrument from the ureter and at least partially retract the instrument from the bladder sufficient to allow the anchor portion to assume a rest state that is larger than the collapsed state. After insertion, the stent can allow fluids from the ureter to pass through the elongated tube from the kidney into the bladder. When the pressure in the bladder increases with fluid from the kidney, the flexible portion between the two valve ends of the flapper valve can move toward the tube port to cover the tube port on the second end and at least partially restrict flow from the bladder to the kidney. After pressure in the bladder is relieved, the flexible portion can return to a rest state and allow flow to resume from the kidney into the bladder. Further, when the elongated tube includes lateral openings, the stent can allow flow between an inside of the elongated tube and an annulus formed outside the periphery of the elongated tube and inside the periphery of the ureter.

Other and further embodiments utilizing one or more aspects of the inventions described above can be devised without departing from the disclosed invention as defined in the claims. For example, different shapes of the anchor portion and the flapper valve could be used, along with other variations that can occur in keeping within the scope of the claims.

The invention has been described in the context of preferred and other embodiments and not every embodiment of the invention has been described. Obvious modifications and alterations to the described embodiments are available to those of ordinary skill in the art. The disclosed and undisclosed embodiments are not intended to limit or restrict the scope or applicability of the invention conceived of by the Applicant, but rather, in conformity with the patent laws, Applicant intends to protect fully all such modifications and improvements that come within the scope or range of equivalents of the following claims.

What is claimed is:

1. A ureteral stent for flow between a kidney and a bladder through a ureter, comprising:
    an elongated tube configured to be inserted into the ureter;
    a first end having a retainer portion configured to be inserted into the kidney; and
    a second end configured to be inserted into the bladder, the second end having an anchor portion fluidicly coupled with the first end, the second end comprising:
        a collapsible wall expandable to a cross-sectional size greater than the cross-sectional size of the ureter;
        a tube port fluidicly coupled with the first end; and
        a flapper valve comprising:
            at least two valve ends coupled to the anchor portion, the at least two valve ends disposed at longitudinally opposite ends of the flapper valve; and
            a flexible middle portion between the at least two valve ends, the flexible middle portion disposed over the tube port and configured to lower toward the tube port to at least partially cover the tube port with a predetermined amount of ambient pressure in the bladder and resume a rest state in an elevated open position away from the tube port when the ambient pressure in the bladder is lower than the predetermined amount.

2. The stent of claim 1, wherein the elongated tube comprises lateral openings along the elongated tube.

3. The stent of claim 1, wherein the stent comprises biocompatible material with at least one polymeric material.

4. The stent of claim 1, wherein a flow path is established between the tube port and the bladder when the flexible middle portion is flexed away from the tube port.

5. The stent of claim 4, wherein the flow path at the end of the tube port is transverse to the flexible middle portion between the at least two valve ends.

6. The stent of claim 1, wherein the anchor portion comprises a base that is expandable to a cross-sectional size greater than the cross-sectional size of the ureter.

7. The stent of claim 1, wherein the anchor portion comprising a base with a sloping surface from the base to the tube port and flapper valve.

8. A method of use for a ureteral stent for flow between a kidney and a bladder through a ureter, the ureteral stent having a first end, an elongated tube coupled to the first end, the first end having a retainer portion, and a second end coupled to the elongated tube distal from the first end, the second end having an anchor portion having a collapsible wall with a flapper valve having at least two valve ends coupled to the anchor portion, the at least two valve ends disposed at longitudinally opposite ends of the flapper valve, and a flexible middle portion between the at least two valve ends, the flexible middle portion disposed over a tube port on the second end from the elongated tube to reciprocally lower toward the tube port and raise away from the tube port, the method comprising:
    reforming the retainer portion of the first end;
    inserting the retainer portion of the first end into a channel of an instrument;
    inserting the instrument into a urethra;
    advancing the first end through the urethra and into the bladder;
    advancing the first end through the ureter and into the kidney with the elongated tube disposed in the ureter and the anchor portion in a collapsed state disposed in the bladder;
    retracting the instrument from the kidney;
    allowing the retainer portion of the first end to assume a rest state in the kidney;
    retracting the instrument from the ureter and at least partially retracting the instrument from the bladder; and
    allowing the anchor portion to assume a rest state that is larger than the collapsed state; and
    allowing the flexible middle portion of the flapper valve to lower toward the tube port to at least partially cover the tube port with a predetermined amount of ambient pressure in the bladder and resume a rest state in an elevated open position away from the tube port to at least partially uncover the tube port when ambient the pressure in the bladder is below the predetermined amount.

9. The method of claim 8, further comprising
    allowing fluids in the kidney to pass through the elongated tube into the bladder and increase pressure in the bladder to move the flexible middle portion toward the tube port to at least partially cover the tube port and at least partially restrict flow from the bladder to the kidney; and allowing the flexible portion to return to the rest state and at least partially uncover the tube port after pressure in the bladder is relieved to resume flow from the kidney into the bladder.

10. The method of claim 8, wherein the elongated tube comprises lateral openings, and further comprising allowing flow between an inside of the elongated tube and an annulus formed outside the periphery of the elongated tube and inside the periphery of the ureter.

* * * * *